(12) United States Patent
He et al.

(10) Patent No.: US 11,667,604 B2
(45) Date of Patent: Jun. 6, 2023

(54) PHENYL CONTAINING COMPOUND, INTERMEDIATE THEREOF, PREPARATION METHOD THEREFOR AND APPLICATION THEREOF

(71) Applicants: SHANGHAI MODERN PHARMACEUTICAL ENGINEERING RESEARCH CENTER CO., LTD., Shanghai (CN); SHANGHAI INSTITUTE OF PHARMACEUTICAL INDUSTRY, Shanghai (CN)

(72) Inventors: Jun He, Shanghai (CN); Zhefeng Wang, Shanghai (CN); Yuezhu Zhao, Shanghai (CN); Yani Yang, Shanghai (CN); Qinghui Fu, Shanghai (CN); Wei Bian, Shanghai (CN); Yuan Zhao, Shanghai (CN); Chen Ge, Shanghai (CN); Yue Zhang, Shanghai (CN); Bing Yi, Shanghai (CN); Minghao Niu, Shanghai (CN); Jiuhui Zhang, Shanghai (CN)

(73) Assignees: SHANGHAI MODERN PHARMACEUTICAL ENGINEERING RESEARCH CENTER CO., LTD., Shanghai (CN); SHANGHAI INSTITUTE OF PHARMACEUTICAL INDUSTRY, Shanghai (CN)

( * ) Notice: Subject to any disclaimer, the term of this patent is extended or adjusted under 35 U.S.C. 154(b) by 0 days.

(21) Appl. No.: 17/627,965

(22) PCT Filed: Jul. 14, 2020

(86) PCT No.: PCT/CN2020/101842
§ 371 (c)(1),
(2) Date: Jan. 18, 2022

(87) PCT Pub. No.: WO2021/008516
PCT Pub. Date: Jan. 21, 2021

(65) Prior Publication Data
US 2022/0274920 A1 Sep. 1, 2022

(30) Foreign Application Priority Data
Jul. 18, 2019 (CN) .......................... 201910650358.1

(51) Int. Cl.
*C07C 309/18* (2006.01)
*A61K 9/107* (2006.01)
(Continued)

(52) U.S. Cl.
CPC .......... *C07C 309/18* (2013.01); *A61K 9/1075* (2013.01); *A61K 31/337* (2013.01); *A61K 47/20* (2013.01); *A61P 35/04* (2018.01)

(58) Field of Classification Search
CPC .... C07C 309/18; A61K 31/337; A61K 47/20; A61K 9/1075
See application file for complete search history.

(56) References Cited

U.S. PATENT DOCUMENTS

2008/0221349 A1  9/2008  Cabaj

FOREIGN PATENT DOCUMENTS

| CN | 1668583 A | 9/2005 |
|---|---|---|
| CN | 101945671 A | 1/2011 |

(Continued)

OTHER PUBLICATIONS

First Office Action issued in the counterpart Chinese application No. 201910650358 dated Sep. 15, 2022.
(Continued)

*Primary Examiner* — Shobha Kantamneni
(74) *Attorney, Agent, or Firm* — Nath, Goldberg & Meyer; Joshua B. Goldberg

(57) ABSTRACT

A phenyl-containing compound, an intermediate thereof, a preparation method therefor and an application thereof. Provided is a compound represented by formula I or a pharmaceutically acceptable salt thereof, where $R^1$, $R^2$, $R^3$, $R^4$ and $R^5$ are independently hydrogen, $C_1$-$C_6$ alkyl, $C_1$-$C_6$ alkoxy or $C(=O)OR^8$; where $R^8$ is $C_1$-$C_4$ alkyl; $R^6$ is (II), (III) or (IV); and $R^7$ is —OH, —NH$_2$, —NHCH$_3$, —N(CH$_3$)$_2$ or $C_{1-4}$ alkoxy. The compound has a low critical micelle concentration (CMC) and good dilution resistance and is capable of enclosing an insoluble drug to form a small-molecule micelle having a high drug loading capacity and good stability.

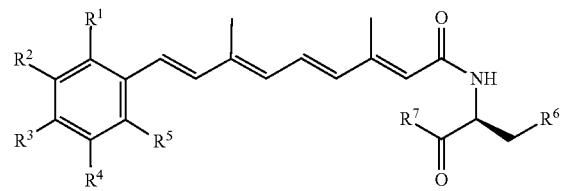

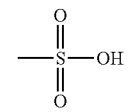

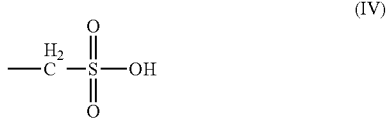

9 Claims, 1 Drawing Sheet

(51) Int. Cl.
*A61K 31/337* (2006.01)
*A61K 47/20* (2006.01)
*A61P 35/04* (2006.01)

(56) References Cited

FOREIGN PATENT DOCUMENTS

| CN | 101951956 A | 1/2011 |
|---|---|---|
| EP | 2116524 A1 | 11/2009 |

OTHER PUBLICATIONS

First Office Action issued in the counterpart Japanese application No. 2022503467 dated Aug. 23, 2022.
Second Office Action issued in the counterpart Chinese application No. 201910650358.1 dated Feb. 2, 2023.
Second Office Action issued in the counterpart Japanese application No. 2022503467 dated Dec. 8, 2022.
International Search Report dated Oct. 15, 2020 Issued in PCT application PCT/CN2020/101842.
Written Opinion of International Searching Authority dated Oct. 12, 2020 Issued in PCT application PCT/CN2020/101842.

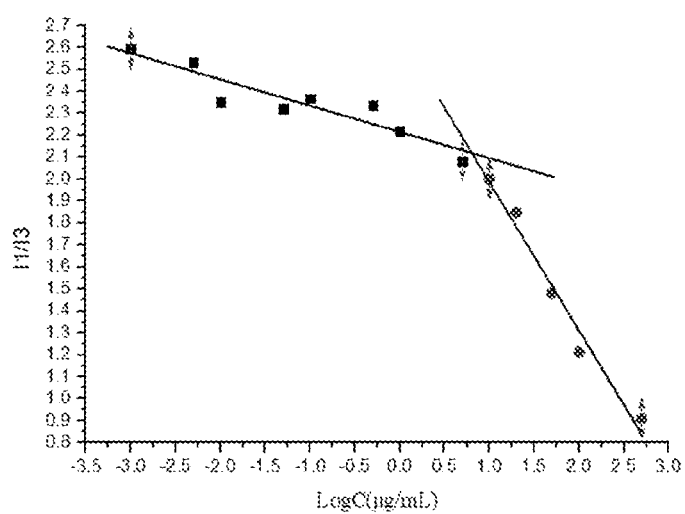

PHENYL CONTAINING COMPOUND, INTERMEDIATE THEREOF, PREPARATION METHOD THEREFOR AND APPLICATION THEREOF

The present application claims the priority of Chinese patent application CN2019106503581 filed on Jul. 18, 2019. The content of the Chinese patent application is hereby incorporated by reference in its entirety.

TECHNICAL FIELD

The present disclosure belongs to the field of pharmacology, and relates to a drug delivery micellar system, specifically relates to a phenyl-containing compound, an intermediate thereof, a preparation method therefor and an application thereof.

BACKGROUND

Micelle system is one of the simplest colloidal drug delivery systems, which can increase the water solubility of insoluble drugs and is a good passive targeting carrier system. The micelles are divided into polymer micelles and small molecule micelles. Through the self-assembly of amphiphilic block copolymers in water, polymer micelles solubilize hydrophobic drug molecules inside micelles, thus prolonging the blood circulation time and half-life of drugs. Commonly, there are polyethylene glycol-polylactic acid block copolymer, polyvinylpyrrolidone-rac-polylactic acid block copolymer, polyoxyethylene-polyoxystyrene block copolymer and polyoxyethylene-polyoxybutylene block copolymer, etc. Small-molecule micelles are less common for drug delivery. Small molecule micelles are formed when the concentration of surfactant is greater than the critical micelle concentration. Surfactant is composed of polar hydrophilic groups and nonpolar hydrophobic groups. Compared with other polymer carriers, small-molecule micelle has high drug loading capacity and good safety.

It is reported in CN1668583A that N-(all-trans-retinoyl)-L-cysteic acid methyl ester and sodium salt thereof can be used as a small molecule micelle. When N-(all-trans-retinoyl)-L-cysteic acid methyl ester and sodium salt thereof are combined with cytotoxic compounds such as docetaxel and doxorubicin, it has synergistic effect: N-(all-trans-retinoyl)-L-cysteic acid methyl ester and sodium salt thereof can prepare drugs with poor solubility (such as docetaxel, paclitaxel, etc.) into water-soluble preparations, which can increase drug solubility and enhance pharmacological activity; N-(all-trans-retinoyl)-L-cysteic acid methyl ester and sodium salt thereof can be prepared into a water-soluble preparation with doxorubicin, which can enlarge the therapeutic window of the drug and improve the therapeutic efficacy.

But N-(all-trans-retinoyl)-L-cysteic acid methyl ester has the disadvantages of poor stability, strong hygroscopicity and cannot be stored in solid form, so it has problems in industrial production and transportation.

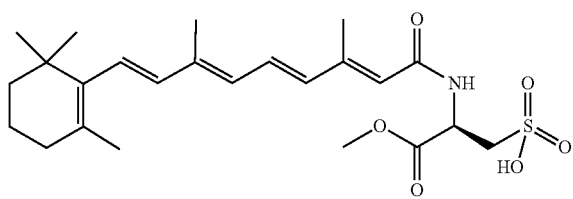

N-(all-trans-retinoyl)-L-cysteic acid methyl ester

Content of the Present Invention

The technical problem to be solved in the present disclosure is to overcome the defect that the existing drug delivery carrier has a single type, and to provide a phenyl-containing compound, an intermediate thereof, a preparation method therefor and an application thereof. The phenyl-containing compound in the present disclosure has low critical micelle concentration (CMC) and good stability.

The present disclosure solves the above technical problem through the following technical solutions.

The present disclosure provides a compound represented by formula I or a pharmaceutically acceptable salt thereof,

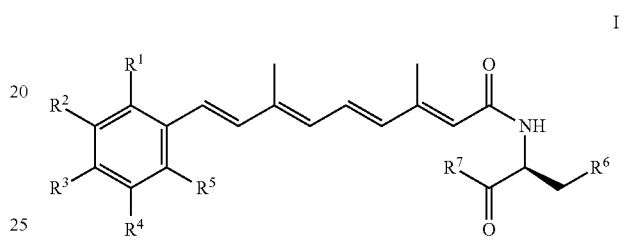

I wherein, $R^1$, $R^2$, $R^3$, $R^4$ and $R^5$ are independently hydrogen, $C_1$-$C_6$ alkyl, $C_1$-$C_6$ alkoxy or $C(=O)OR^8$; wherein $R^8$ is $C_1$-$C_4$ alkyl;

$R^6$ is

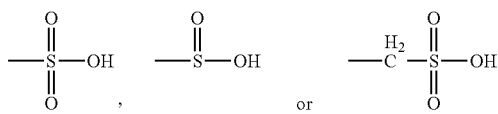

(correspondingly, in the pharmaceutically acceptable salt of the compound represented by formula I, $R^6$ can be

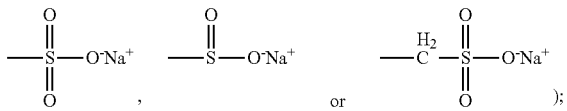

);

$R^7$ is —OH, —NH$_2$, —NHCH$_3$, —N(CH$_3$)$_2$ or $C_{1-4}$ alkoxy (correspondingly, in the pharmaceutically acceptable salt of the compound represented by formula I, $R^7$ can be —O$^-$Na$^+$).

In a preferred embodiment of the present disclosure, when the $R^1$, $R^2$, $R^3$, $R^4$ and $R^5$ are independently $C_1$-$C_6$ alkyl, the $C_1$-$C_6$ alkyl is preferably $C_1$-$C_4$ alkyl, more preferably methyl, ethyl, n-propyl, isopropyl, n-butyl, isobutyl or tert-butyl, further preferably methyl.

In a preferred embodiment of the present disclosure, when the $R^1$, $R^2$, $R^3$, $R^4$ and $R^5$ are independently $C_1$-$C_6$ alkoxy, the $C_1$-$C_6$ alkoxy is preferably $C_1$-$C_4$ alkoxy, more preferably methoxy, ethoxy, n-propoxy, isopropoxy, n-butoxy, isobutoxy or tert-butoxy, further preferably methoxy.

In a preferred embodiment of the present disclosure, the $R^8$ is preferably methyl, ethyl, n-propyl, isopropyl, n-butyl, isobutyl or tert-butyl.

In a preferred embodiment of the present disclosure, the $R^6$ is preferably

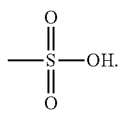

In a preferred embodiment of the present disclosure, when the $R^7$ is $C_1$-$C_4$ alkoxy, the $C_1$-$C_4$ alkoxy is preferably methoxy, ethoxy, n-propoxy, isopropoxy, n-butoxy, isobutoxy or tert-butoxy, more preferably methoxy.

In a preferred embodiment of the present disclosure, the $R^7$ is preferably $C_1$-$C_4$ alkoxy.

In a preferred embodiment of the present disclosure, the $R^1$, $R^2$ and $R^5$ are independently $C_1$-$C_6$ alkyl; the $R^3$ is $C_1$-$C_6$ alkoxy; the $R^4$ is hydrogen; the $R^6$ is

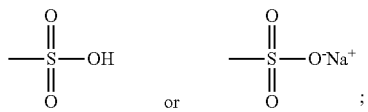

the $R^7$ is $C_{1-4}$ alkoxy.

In a preferred embodiment of the present disclosure, the compound represented by formula I or the pharmaceutically acceptable salt thereof is preferably

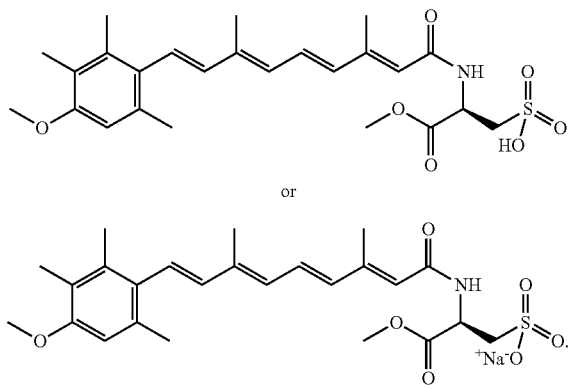

The present disclosure also provides a preparation method of the compound represented by formula I, comprising the following steps: In a polar aprotic solvent, in the presence of a base, a compound represented by formula III and a compound represented by formula II are subjected to the following amine transesterification reaction,

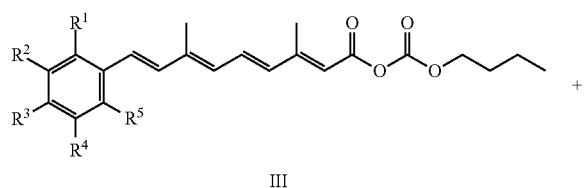

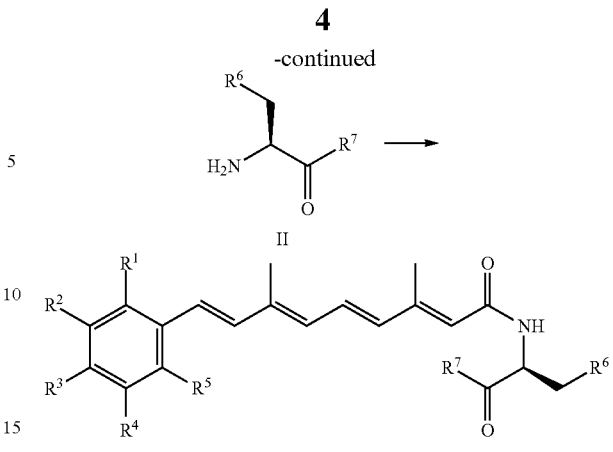

wherein, $R^1$, $R^2$, $R^3$, $R^4$, $R^5$, $R^6$ and $R^7$ are as defined above.

In the amine transesterification reaction, the polar aprotic solvent can be a conventional polar aprotic solvent for such reactions in the art, and particularly preferably one or more of an amide solvent, an ether solvent, a ketone solvent, a nitrile solvent and a sulfoxide solvent in the present disclosure. The amide solvent is preferably one or more of N,N-dimethylformamide, hexamethylphosphoramide and N,N-dimethylacetamide, and more preferably N,N-dimethylformamide. The ether solvent is preferably tetrahydrofuran. The ketone solvent is preferably acetone and/or N-methylpyrrolidone. The nitrile solvent is preferably acetonitrile. The sulfoxide solvent is preferably dimethyl sulfoxide. The polar aprotic solvent is preferably an amide solvent, an ether solvent and a nitrile solvent, more preferably tetrahydrofuran, acetonitrile and N,N-dimethylformamide.

In the amine transesterification reaction, the molar concentration of the compound represented by formula III in the polar aprotic solvent can be a conventional molar concentration for such reactions in the art, particularly preferably 0.01 to 0.2 mol/L, more preferably 0.05 to 0.8 mol/L (e.g., 0.0625 mol/L) in the present disclosure.

In the amine transesterification reaction, the base can be a conventional base for such reactions in the art, particularly preferably an organic amine, more preferably one or more of triethylamine, diisopropylethylamine, pyridine, tri-n-butylamine and N-methylmorpholine, and further preferably triethylamine in the present disclosure.

In the amine transesterification reaction, the molar ratio of the base to the compound represented by formula III can be a conventional molar ratio for such reactions in the art, particularly preferably 1.5:1 to 3:1, more preferably 1.8:1 to 2.5:1 (e.g., 2.02:1) in the present disclosure.

In the amine transesterification reaction, the molar ratio of the compound represented by formula II to the compound represented by formula III can be a conventional molar ratio for such reactions in the art, particularly preferably 1:1 to 3:1, more preferably 1:1 to 2:1 (e.g., 1.5:1) in the present disclosure.

In the amine transesterification reaction, the process of the reaction can be monitored using conventional monitoring methods in the art (e.g., TLC, HPLC, or NMR), generally with the detection of the disappearance of the compound represented by formula III as the end point of the reaction. The reaction time of the reaction is preferably 1 to 24 hours, more preferably 4 to 12 hours (e.g., 4 hours and 12 hours).

In the amine transesterification reaction, the reaction temperature of the reaction can be a conventional reaction temperature for such reactions in the art, particularly preferably room temperature in the present disclosure.

In the amine transesterification reaction, the reaction further comprises a post-treatment step after the end of the reaction. The post-treatment steps are preferably concentration, quenching, extraction, re-extraction, washing, filtration and drying of the reaction solution. The reagent used for the quenching is preferably water. The reagent used for the extraction is preferably methyl tert-butyl ether. The reagent used for the re-extraction is preferably ethyl acetate. The reagent used for the washing is preferably saturated sodium chloride solution. The temperature of the drying is preferably 40° C. The instrument used for the drying is preferably a vacuum drying oven.

In a preferred embodiment of the present disclosure, the preparation method of the compound represented by formula I comprises the following steps: the polar aprotic solvent, the base and the compound represented by formula II are mixed, and the compound represented by formula III is added to carry out the reaction.

The present disclosure also provides a preparation method of the compound represented by formula I, the method can further comprise the following steps: in a polar aprotic solvent, in the presence of a base, a compound represented by formula IV and a compound represented by formula V are subjected to the following condensation reaction,

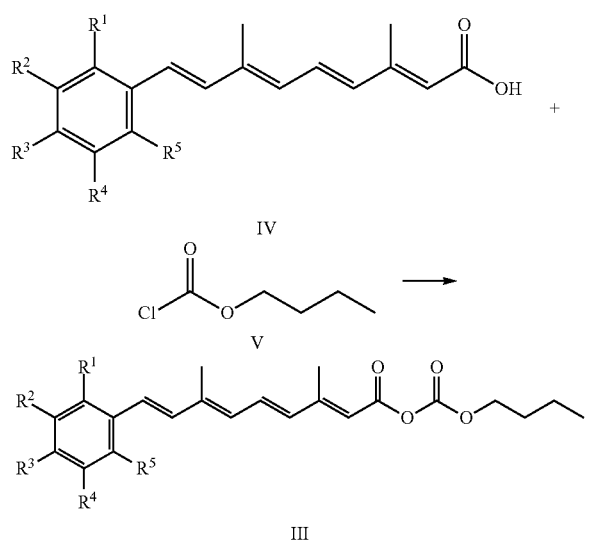

wherein, $R^1$, $R^2$, $R^3$, $R^4$ and $R^5$ are as defined above.

In the condensation reaction, the polar aprotic solvent can be a conventional polar aprotic solvent for such reactions in the art, particularly preferably an ether solvent and/or a nitrile solvent, preferably an ether solvent and a nitrile solvent, more preferably an ether solvent and a nitrile solvent with a volume ratio of 1:2 in the present disclosure. The ether solvent is preferably tetrahydrofuran. The nitrile solvent is preferably acetonitrile. The polar aprotic solvent is preferably a mixed solvent of tetrahydrofuran and acetonitrile with a volume ratio of 1:2.

In the condensation reaction, the molar concentration of the compound represented by formula IV in the polar aprotic solvent can be a conventional molar concentration for such reactions in the art, particularly preferably 0.01 to 1 mol/L, and more preferably 0.1 to 0.2 mol/L (e.g., ⅙ mol/L) in the present disclosure.

In the condensation reaction, the base can be a conventional base for such reactions in the art, particularly preferably an organic amine, more preferably one or more of triethylamine, diisopropylethylamine, pyridine, tri-n-butylamine and N-methylmorpholine, and further preferably triethylamine in the present disclosure.

In the condensation reaction, the molar ratio of the base to the compound represented by formula IV can be a conventional molar ratio for such reactions in the art, particularly preferably 1:1 to 3:1, more preferably 1:1 to 1.5:1 (e.g., 1.15:1) in the present disclosure.

In the condensation reaction, the molar ratio of the compound represented by formula V to the compound represented by formula IV can be a conventional molar ratio for such reactions in the art, particularly preferably 1:1 to 3:1, and more preferably 1:1 to 1.5:1 (e.g., 1.1:1) in the present disclosure.

In the condensation reaction, the process of the reaction can be monitored using conventional monitoring methods in the art (e.g., TLC, HPLC, or NMR), generally with the detection of the disappearance of the compound represented by formula IV as the end point of the reaction. The reaction time of the reaction is preferably 10 to 60 minutes, more preferably 25 to 35 minutes (e.g., 30 minutes).

In the condensation reaction, the reaction temperature of the reaction can be a conventional reaction temperature for such reactions in the art, particularly preferably 0 to −40° C., and more preferably −10 to −30° C. (e.g., −20° C.) in the present disclosure.

In a preferred embodiment of the present disclosure, the condensation reaction comprises the following steps: the polar aprotic solvent, the base and the compound represented by formula IV are mixed, and the compound represented by formula V is added to carry out the reaction.

The present disclosure also provides a compound represented by formula III,

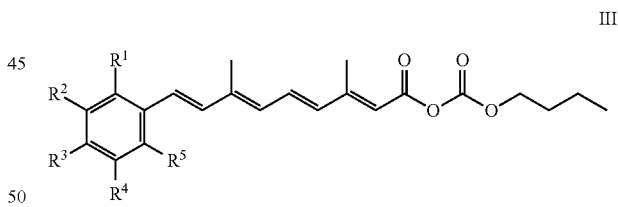

wherein, $R^1$, $R^2$, $R^3$, $R^4$ and $R^5$ are as defined above.

In a preferred embodiment of the present disclosure, the compound represented by formula III is preferably

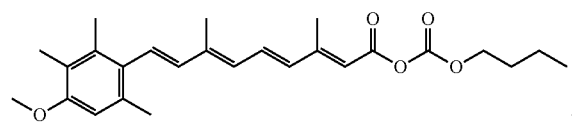 [SMILES: CCCCOC(=O)OC(=O)/C=C(C)/C=C/C=C(C)/C=C/c1c(C)cc(OC)c(C)c1C]

The present disclosure also provides an application of the compound represented by formula I or the pharmaceutically acceptable salt thereof as a pharmaceutical excipient.

The pharmaceutical excipient is preferably a drug carrier in a micellar drug delivery system. The drug in the drug carrier is preferably a hydrophobic drug. The hydrophobic drug is preferably docetaxel, doxorubicin or paclitaxel, and further preferably docetaxel.

The present disclosure also provides a hydrophobic drug micelle, the hydrophobic drug micelle comprises the hydrophobic drug and a substance X; the substance X is the compound represented by formula I or the pharmaceutically acceptable salt thereof.

In a preferred embodiment of the present disclosure, in the hydrophobic drug micelles, the mass ratio of the hydrophobic drug to the substance X is preferably 1.25:1 to 3:1.

The present disclosure also provides a preparation method of the hydrophobic drug micelles, the method comprises the following steps:

Step 1: Mixing the hydrophobic drug, the substance X and methanol to obtain a material A;

Step 2: Removing methanol from the material A, hydrating, filtering and freeze-drying.

In a preferred embodiment of the present disclosure, in the preparation method of the hydrophobic drug micelles, the mass ratio of the substance X to the hydrophobic drug is preferably 1.25:1 to 3:1.

In a preferred embodiment of the present disclosure, the volume of the methanol is sufficient to dissolve the hydrophobic drug, the ratio of the volume of the methanol to the mass of the hydrophobic drug is preferably 1:4 mL/g.

In a preferred embodiment of the present disclosure, in step 1: after mixing the hydrophobic drug, the substance X and methanol, further comprising an ultrasonic step, and the material A is obtained after the ultrasonic step.

In a preferred embodiment of the present disclosure, the method for removing methanol is preferably rotary evaporation and drying. The temperature of the rotary evaporation is preferably 30° C. to 50° C. (e.g., 40° C.). The temperature of the drying is preferably 30° C. to 50° C. (e.g., 40° C.).

In a preferred embodiment of the present disclosure, the ratio of the volume of the water for injection used for the hydration to the mass of the hydrophobic drug is preferably 1:10 mL/g to 3:10 mL/g, more preferably 1:10 mL/g, 3:20 mL/g, 1:5 mL/g, 1:4 mL/g or 3:10 mL/g.

In a preferred embodiment of the present disclosure, the speed of hydration can be a conventional speed for hydration in film hydration in the art, particularly preferably 100 to 200 r/min (e.g., 100 r/min) in the present disclosure.

In a preferred embodiment of the present disclosure, the time of hydration can be a conventional time for hydration in thin film hydration method in the art, particularly preferably 5 to 20 min (e.g., 10 min) in the present disclosure.

In a preferred embodiment of the present disclosure, the filter used for the filtration is preferably a microporous filter membrane. The pore size of the microporous filter membrane is preferably 0.22 μm.

The present disclosure also provides a hydrophobic pharmaceutical micelle prepared according to the above preparation method; the hydrophobic drug is preferably docetaxel.

The present disclosure also provides an application of docetaxel micelles in the preparation of a medicament for treating advanced or metastatic breast cancer that has failed prior chemotherapy, or advanced or metastatic non-small cell lung cancer drugs that has failed cisplatin-based chemotherapy.

In the present disclosure, room temperature refers to 10 to 30° C.

In the present disclosure, hydrophobic drug refers to drug that tend to be non-polar, are insoluble in water, and are easily dissolved in neutral and non-polar solutions (such as organic solvents). The hydrophobic drugs include but are not limited to docetaxel, doxorubicin or paclitaxel.

On the basis of not violating the common sense in the art, the above-mentioned preferred conditions can be arbitrarily combined to obtain the preferred embodiments of the present disclosure.

The reagents and raw materials used in the present disclosure are commercially available.

The positive progressive effect of the present disclosure is that: the phenyl-containing compound provided in the present disclosure has a low critical micelle concentration (CMC), good dilution resistance, can wrap insoluble drugs to form small molecule micelles, has a high drug loading capacity and good stability.

BRIEF DESCRIPTION OF THE DRAWINGS

FIG. 1 shows the determination of CMC value of carrier by pyrene fluorescence probe method.

DETAILED DESCRIPTION OF THE PREFERRED EMBODIMENT

The following embodiments further illustrate the present disclosure, but the present disclosure is not limited thereto. The experimental methods not specified in the specific conditions in the following embodiments are selected according to the conventional methods and conditions, or according to the commodity instructions.

Embodiment 1

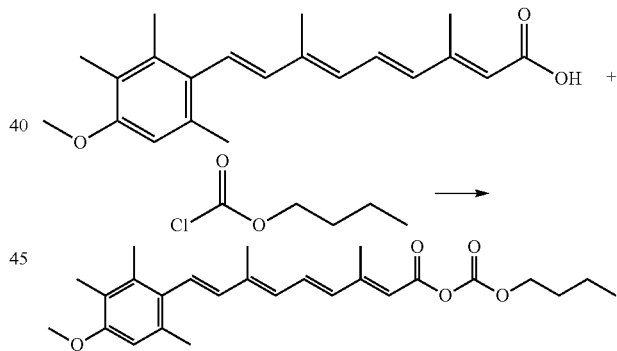

Preparation of acitretin butyric anhydride: In a 25 mL three-necked flask, acitretin (0.32 g, 1 mmol), 2 mL of tetrahydrofuran, 4 mL of acetonitrile, and 0.16 mL of triethylamine were added in sequence at room temperature. The flask was put into a low temperature cooling tank with mechanical stirring, when the reaction system was cooled to −20° C., butyl chloroformate (0.14 mL, 1.1 mmol) was slowly added, after the addition was completed, the reaction was continued for 30 min. A reaction solution of acitretin butyric anhydride was obtained.

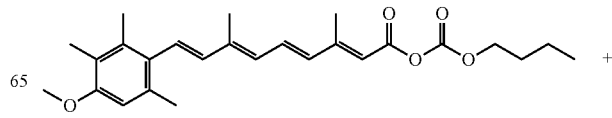

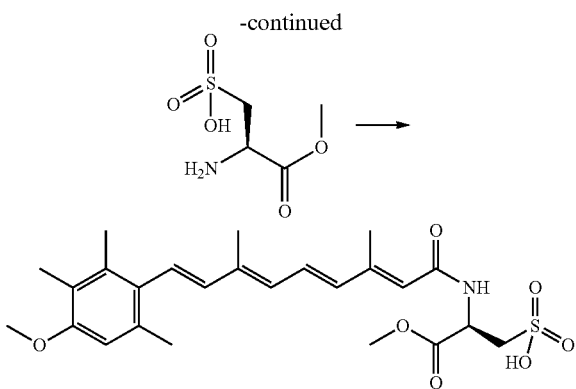

Preparation of carrier: In a 25 mL four-necked flask, at room temperature, L-cysteic acid methyl ester (0.33 g, 1.5 mmol), 10 mL of N,N-dimethylformamide, 0.26 mL of triethylamine were added, the mixture was mechanically stirred at room temperature until the solid in the mixture was almost dissolved, and then the reaction solution of acitretin butyric anhydride was added dropwise. After the dropwise addition was completed, the reaction was continued for 4 hours. After the reaction was completed, part of the solvent was spun off, 20 mL of water was added, and the unreacted acitretin was extracted with methyl tert-butyl ether (20 mL×3), and the reaction product was extracted with ethyl acetate (20 mL×2). The ethyl acetate phase was washed with saturated sodium chloride, and the solid was precipitated for the second time. After filtration, the solid was placed in a 40° C. vacuum drying oven to obtain 410 mg of light yellow solid. The yield of the product was 84%, and the purity was 99.78%.

Preparation of sodium salt carrier: In a 25 mL four-necked flask, at room temperature, L-cysteic acid methyl ester (0.33 g, 1.5 mmol), 10 mL of N,N-dimethylformamide, 0.26 mL of triethylamine were added, the mixture was mechanically stirred at room temperature until the solid in the mixture was almost dissolved, and then the reaction solution of acitretin butyric anhydride was added dropwise. After the dropwise addition was completed, the reaction was continued for 4 hours. After the reaction was completed, part of the solvent was spun off, 6 mL of saturated sodium bicarbonate was added, the mixture was continued to stir for 1 hour, 20 mL of water was added, the unreacted acitretin was extracted with methyl tert-butyl ether (20 mL×3), and the reaction product was extracted with ethyl acetate (20 mL×2). The ethyl acetate phase was washed with saturated sodium chloride, and the solid was precipitated for the second time. After filtration, the solid was placed in a 40° C. vacuum drying oven to obtain 410 mg of light yellow solid. The yield of the product was 82%, and the purity was 99.64%.

Carrier: MS (ESI) m/z 490.29 (M-H$^+$); $^1$H NMR (400 MHz, MeOD) δ8.00 (s, 1H, NH), 7.06 (dd, J=14.9, 11.5 Hz, 1H, CH═CH—), 6.72 (d, J=16.3 Hz, 1H, —CH═CH—), 6.65 (s, 1H, Ph-H), 6.38 (d, J=15.0 Hz, 1H, —CH═CH—), 6.32-6.19 (m, 2H, —CH═CH—), 4.58 (s, 1H, CH), 3.77 (s, 3H, C—O—CH$_3$), 3.02 (s, 1H, CH$_2$), 2.88 (s, 1H, CH$_2$), 2.33 (s, 3H, CH$_3$), 2.29 (s, 3H, CH$_3$), 2.23 (s, 3H, CH$_3$), 2.12 (s, 6H, CH$_3$).

Carrier: HPLC detection conditions: chromatographic column: Inertsil ODS-SP (4.6×250 mm, 5 μm); mobile phase: acetonitrile: phosphate buffer salt (43:57); buffer: 20 mmol/L potassium dihydrogen phosphate and disodium hydrogen phosphate; flow rate: 1.0 mL/min; column temperature: 40° C.; detection wavelength: 355 nm; injection volume: 10 μL; retention time of product peak: 21.234 min. See Table 1 for details of HPLC detection results.

TABLE 1

HPLC detection results of carriers

| Peak | Retention time min | Peak width (5%) min | Peak area | Peak height mV | Relative peak area % |
|---|---|---|---|---|---|
| 1 | 5.069 | 0.306 | 14786 | 1597 | 0.0635 |
| 2 | 6.201 | 0.418 | 8840 | 786 | 0.0380 |
| 3 | 7.060 | 0.000 | 2837 | 231 | 0.0122 |
| 4 | 19.058 | 0.000 | 5918 | 284 | 0.0254 |
| 5 | 19.436 | 0.000 | 13409 | 502 | 0.0576 |
| 6 | 21.234 | 1.162 | 23215820 | 642027 | 99.7804 |
| 7 | 26.923 | 0.000 | 5309 | 157 | 0.0228 |

Embodiment 2

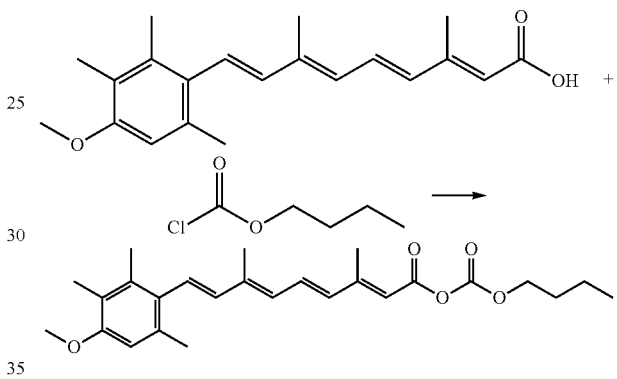

Preparation of acitretin butyric anhydride: In a 50 mL three-necked flask, acitretin (0.98 g, 3 mmol), 6 mL of tetrahydrofuran, 12 mL of acetonitrile, and 0.48 mL of triethylamine were added in sequence at room temperature. The flask was put into a low temperature cooling tank with mechanical stirring; when the reaction system was cooled to −20° C., butyl chloroformate (0.42 mL, 3.3 mmol) was slowly added; after the addition was completed, the reaction was continued for 30 min. A reaction solution of acitretin butyric anhydride was obtained.

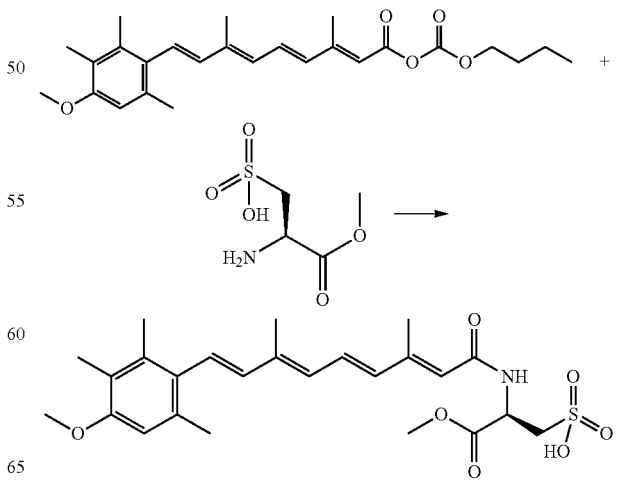

Preparation of carrier: In a 100 mL four-necked flask, at room temperature, L-cysteic acid methyl ester (0.99 g, 4.5 mmol), 30 mL of N,N-dimethylformamide, 0.78 of mL triethylamine were added, the mixture was mechanically stirred at room temperature until the solid in the mixture was almost dissolved, and then the reaction solution of acitretin butyric anhydride was added dropwise. After the dropwise addition was completed, the reaction was continued for 12 hours. After the reaction was completed, part of the solvent was spun off, 60 mL of water was added, the unreacted acitretin was extracted with methyl tert-butyl ether (60 mL×3), and the reaction product was extracted with ethyl acetate (60 mL×3). The ethyl acetate phase was washed with saturated sodium chloride, and the solid was precipitated for the second time. After filtration, the solid was placed in a 40° C. vacuum drying oven to obtain 1.21 g of light yellow solid. The yield of the product was 82% and the purity was 99.69%. The MS (ESI) and $^1$H NMR data were the same as the carrier of embodiment 1.

Embodiment 3 Determination of Critical Micelle Concentration (CMC) by Pyrene Fluorescence Probe Method 1.0 mg/mL pyrene mother liquor was diluted 100 times to 0.01 mg/mL with acetone, then 10 µL of diluent was transferred into 1.5 mL EP tube, and the acetone was evaporated in a ventilated place at room temperature and away from light. 1 mL of carrier solution with different concentrations (the carrier of embodiment 1 was dissolved in pure water and configured to different concentrations) was added, and the mixture was shaken and equilibrated for 6 hours. The fluorescence intensity values at I1 (373 nm) and I3 (384 nm) were measured by fluorescence spectrophotometer, and the CMC was measured to be 6.5 µg/mL by plotting LogC with I1/I3.

Embodiment 4 Stability Testing of Carriers

The carrier of embodiment 1 was placed in solid form under normal temperature and normal light, normal temperature and away from light, 4° C. away from light and −18° C. away from light, respectively, and the residual amount of the carrier was measured after being placed for 1d, 3d, 7d, 30d, 60d, 90d and 120d, respectively, and the residual amount was determined by HPLC. The test results are shown in Table 2.

TABLE 2

Stability data of the carrier of Embodiment 1

|  | Normal temperature and normal light (%) | Normal temperature and away from light (%) | 4° C. Away from light (%) | −18° C. Away from light (%) |
|---|---|---|---|---|
| 0 d | 99.87 | 99.87 | 99.87 | 99.87 |
| 1 d | 99.24 | 99.34 | 99.57 | 99.7 |
| 3 d | 99.11 | 99.13 | 99.3 | 99.69 |
| 7 d | 99.09 | 99.12 | 99.25 | 99.61 |
| 30 d | 98.99 | 98.97 | 99.26 | 99.54 |
| 60 d | 98.91 | 98.93 | 99.16 | 99.51 |
| 90 d | 98.85 | 98.55 | 99.05 | 99.45 |
| 120 d | 98.84 | 98.19 | 99.04 | 99.21 |

Embodiment 5 Preparation of Docetaxel Nano Micelles by Thin Film Hydration Method Docetaxel (DTX), the carrier of embodiment 1 were weighed, the mixture was sonicated with methanol until the solid was completely dissolved, placed in a vacuum drying oven at 40° C. for 5 min to remove the solvent methanol, and then the residue was placed in vacuum drying oven at 40° C. for 2 hours to remove the residual solvent, water for injection was added for hydration, wherein hydration speed was 100 r/min, hydration time was 10 min, the mixture was filtered with 0.22 µm microporous filter membrane (PES), and freeze-dried to obtain nano micelle freeze-dried preparation. The characterization data of the preparation are shown in Table 3.

TABLE 3

Characterization data of formulations with different mass ratios of docetaxel and carrier

| Number | DTX (mg) | Carrier (mg) | Methanol (mL) | Water for injection (mL) | Particle size | Polymer dispersion index | Encapsulation rate (%) | Drug loading capacity |
|---|---|---|---|---|---|---|---|---|
| 1 | 20 | 25 | 5 | 4 | 14.01 | 0.232 | 99.34 | 42.01 |
| 2 | 20 | 30 | 5 | 4 | 15.41 | 0.199 | 99.78 | 40.02 |
| 3 | 20 | 35 | 5 | 4 | 13.84 | 0.186 | 99.26 | 35.03 |
| 4 | 20 | 40 | 5 | 4 | 12.31 | 0.173 | 99.76 | 32.46 |
| 5 | 20 | 50 | 5 | 4 | 12.29 | 0.168 | 99.76 | 27.87 |
| 6 | 20 | 60 | 5 | 4 | 16.64 | 0.464 | 99.90 | 25.38 |

Embodiment 6 Preparation of Docetaxel Nano Micelles by Thin Film Hydration Method 20 mg of Docetaxel (DTX), 30 mg of the carrier of embodiment 1 were weighed, the mixture was sonicated with 5 mL of methanol until the solid was completely dissolved, placed in a vacuum drying oven at 40° C. for 5 min to remove the solvent methanol, and then the residue was placed in vacuum drying oven at 40° C. for 2 hours to remove the residual solvent, water for injection was added for hydration, wherein hydration speed was 100 r/min, hydration time was 10 min, the mixture was filtered with 0.22 µm microporous filter membrane (PES), and freeze-dried to obtain nano micelle freeze-dried preparation. The characterization data of the preparation are shown in Table 4.

TABLE 4

Characterization data of preparation under different volumes of water for injection

| Number | Water for injection (mL) | Particle size | Polymer dispersion index | Encapsulation rate (%) | Drug loading capacity |
|---|---|---|---|---|---|
| 1 | 2 | 16.93 | 0.185 | 98.70 | 39.09 |
| 2 | 3 | 18.98 | 0.235 | 99.72 | 38.50 |
| 3 | 4 | 19.18 | 0.187 | 99.81 | 39.71 |
| 4 | 5 | 16.87 | 0.277 | 98.79 | 38.15 |
| 5 | 6 | 18.62 | 0.200 | 99.72 | 40.34 |

Comparative Embodiment 1

The sodium salt of N-(all-trans-retinoyl)-L-cysteic acid methyl ester was placed in solid form at normal temperature and normal light, at normal temperature and away from light, at 4° C. away from light and at −18° C. away from light respectively (other conditions are the same as those in embodiment 4), and the appearance and residual amount were tested after being placed for 1d, 3d, 7d and 30d, respectively, wherein the residual amount was determined by HPLC. The test results are shown in Table 5.

TABLE 5

Stability data of sodium salt of N-(all-trans-retinoyl)-L-cysteic acid methyl ester

| | Appearance | Normal temperature and normal light (%) | Normal temperature and away from light (%) | 4° C. Away from light (%) | −18° C. Away from light (%) |
|---|---|---|---|---|---|
| 0 d | Yellow powder | 99.54 | 99.54 | 99.54 | 99.54 |
| 3 d | Orange | 83.71 | 88.91 | 93.76 | 96.16 |
| 7 d | Brown viscous | 64.32 | 78.62 | 89.09 | 94.17 |
| 30 d | Dark brown viscous | — | — | 79.69 | 89.98 |

Although the above describes specific embodiments of the present disclosure, it should be understood by those skilled in the art that these are merely illustrative examples and that a variety of changes or modifications to these embodiments can be made without departing from the principles and substance of the present disclosure. Therefore, the scope of protection of the present disclosure is limited by the appended claims.

What is claimed is:

1. A compound of formula I or a pharmaceutically acceptable salt thereof,

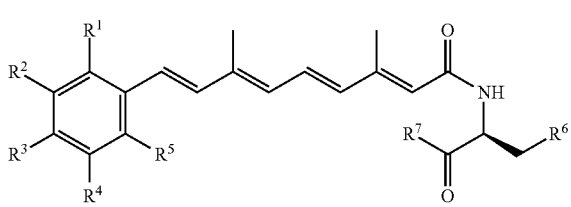

wherein, $R^1$, $R^2$, $R^3$, $R^4$ and $R^5$ are independently hydrogen, $C_1$-$C_6$ alkyl, $C_1$-$C_6$ alkoxy or $C(=O)OR^8$; wherein $R^8$ is $C_1$-$C_4$ alkyl;

$R^6$ is

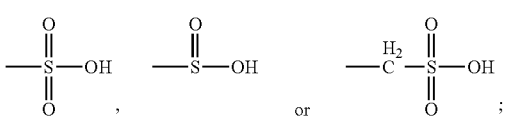

$R^7$ is —OH, —$NH_2$, —$NHCH_3$, —$N(CH_3)_2$ or $C_{1-4}$ alkoxy.

2. The compound of formula I or the pharmaceutically acceptable salt thereof according to claim 1, wherein, in the pharmaceutically acceptable salt of the compound of formula I, $R^6$ of the compound of formula I forms

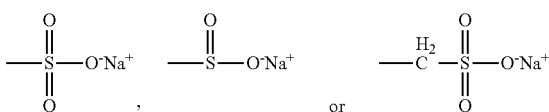

with sodium ion;

or, in the pharmaceutically acceptable salt of the compound of formula I, when $R^7$ of the compound of formula I is —OH, it forms —O⁻Na⁺ with sodium ion;

or, when the $R^1$, $R^2$, $R^3$, $R^4$ and $R^5$ are independently $C_1$-$C_6$ alkyl, the $C_1$-$C_6$ alkyl is $C_1$-$C_4$ alkyl;

or, when the $R^1$, $R^2$, $R^3$, $R^4$ and $R^5$ are independently $C_1$-$C_6$ alkoxy, the $C_1$-$C_6$ alkoxy is $C_1$-$C_4$ alkoxy;

or, the $R^8$ is methyl, ethyl, n-propyl, isopropyl, n-butyl, isobutyl or tert-butyl;

or, when the $R^7$ is independently $C_1$-$C_4$ alkoxy, the $C_1$-$C_4$ alkoxy is methoxy, ethoxy, n-propoxy, isopropoxy, n-butoxy, isobutoxy or tert-butoxy, or, the $R^6$ is

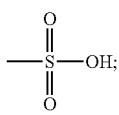

or, the $R^7$ is $C_{1-4}$ alkoxy.

3. The compound of formula I or the pharmaceutically acceptable salt thereof according to claim 1, wherein, the compound formula I or the pharmaceutically acceptable salt thereof is

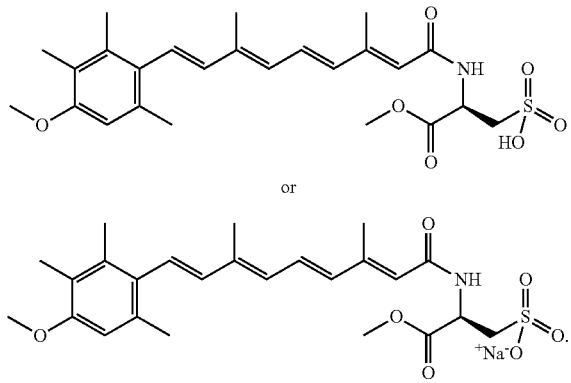

4. A preparation method of the compound of formula I according to claim 1, wherein, the method comprises the following steps: in a polar aprotic solvent, in the presence of a base, a compound of formula III and a compound of formula II are subjected to the following amine transesterification reaction,

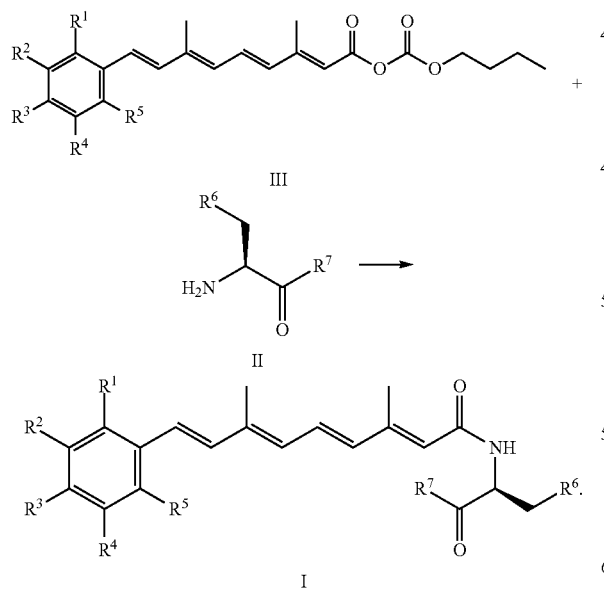

5. The preparation method of the compound of formula I according to claim 4, wherein, the method further comprises the following steps: in a polar aprotic solvent, in the presence of a base, a compound of formula IV and a compound of formula V are subjected to the following condensation reaction,

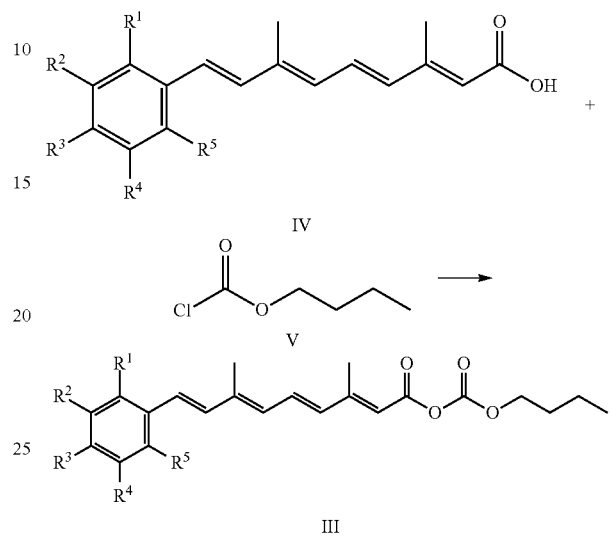

6. A compound of formula III,

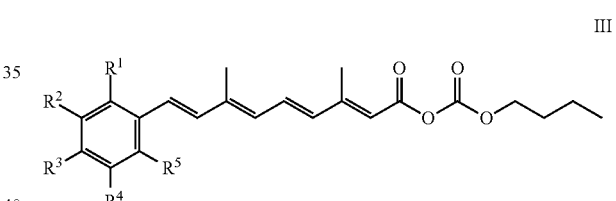

wherein, $R^1$, $R^2$, $R^3$, $R^4$ and $R^5$ are as defined in claim 1.

7. The compound of formula III according to claim 6, wherein, the compound of formula III is

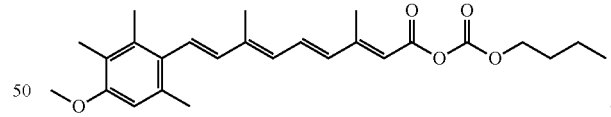

8. A hydrophobic drug micelles, wherein, the hydrophobic drug micelle comprises a hydrophobic drug and a substance X; the substance X is the compound of formula I or the pharmaceutically acceptable salt thereof according to claim 1, wherein the hydrophobic drug is docetaxel, doxorubicin or paclitaxel.

9. The hydrophobic drug micelles according to claim 8, wherein, the mass ratio of the hydrophobic drug to the substance X is 1.25:1 to 3:1.

* * * * *